United States Patent [19]

Trampert

[11] 4,166,020
[45] Aug. 28, 1979

[54] MEASURING PROBE TO DETERMINE THE ION CONCENTRATION IN LIQUIDS

[75] Inventor: Hans R. Trampert, Oftersheim, Fed. Rep. of Germany

[73] Assignee: Pfaudler-Werke A.G., Schwetzingen, Fed. Rep. of Germany

[21] Appl. No.: 903,619

[22] Filed: May 8, 1978

[30] Foreign Application Priority Data

May 14, 1977 [DE] Fed. Rep. of Germany ....... 2721939

[51] Int. Cl.² ............................................. G01N 27/30
[52] U.S. Cl. ........................... 204/195 R; 204/195 G; 204/195 F
[58] Field of Search ........... 204/195 G, 195 F, 195 R; 324/30 R, 29; 128/2 E

[56] References Cited
U.S. PATENT DOCUMENTS 3,787,307  1/1974  Schwab et al. .................. 204/195 G Primary Examiner—G. L. Kaplan
Attorney, Agent, or Firm—Theodore B. Roessel; J. Stephen Yeo

[57] ABSTRACT

A combination pH electrode uses an enameled steel structure. The reference electrode is replaceable and may be interchanged with a different type of electrode or a sealing plug.

5 Claims, 1 Drawing Figure

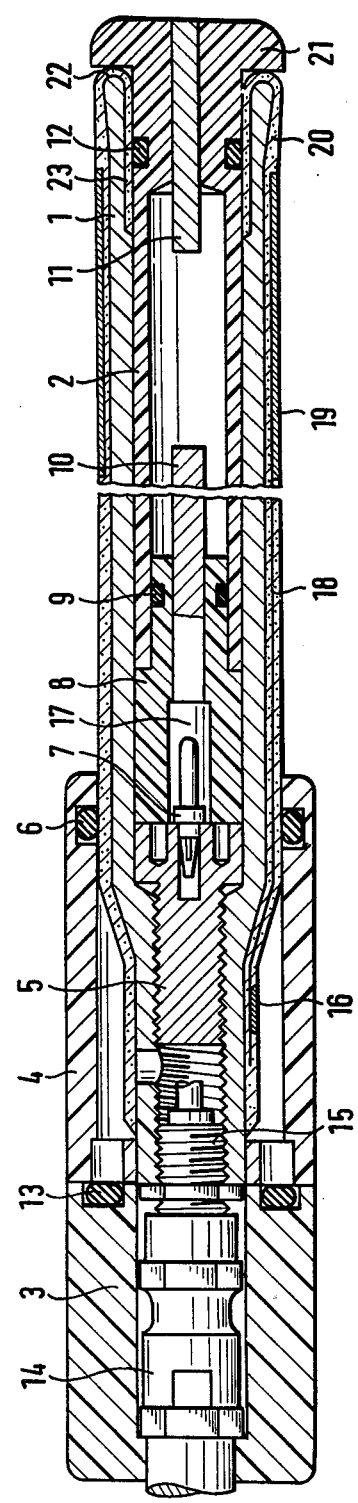

MEASURING PROBE TO DETERMINE THE ION CONCENTRATION IN LIQUIDS

BACKGROUND OF THE INVENTION

The invention concerns a measuring probe for the determination of ion concentrations in liquids, for pH measurements and the like.

U.S. Pat. No. 3,787,307 describes a measuring probe wherein the steel tube carrying the measuring probe is glass-lined on the inside and the outside and surrounds an enameled, rod-like steel body carrying the reference electrode. The lower end of the steel rod is widened in such a manner that a junction may be inserted between the adjoining enameled surfaces, through which junction the reference liquid may be brought into contact with the liquid to be measured. Compared with the familiar single rod measuring systems (combination electrodes) with glass electrodes, such measuring probes have the advantage of being sufficiently mechanically stable, thereby making possible measurement of the pH-value in chemical vessels with running agitators where considerable mechanical stresses occur. The use of mechanically sensitive single rod measuring systems in pipe lines with high flow velocities or in high viscosity liquids or liquids containing solids, necessitates application of special protective devices, such as protective baskets, sheet metal baffles or wire lattices. These devices may result in delayed indication, falsified measuring values or in extreme cases even a non-functioning of the single rod measuring systems. A disadvantage of the familiar enameled probes is that they cannot be manufactured with a diameter as small as 12 mm so as to replace mechanically sensitive combination electrodes having such a small diameter.

It is therefore the purpose of the invention to improve an enameled measuring probe as described above, largely avoiding the described drawbacks and difficulties, providing—a mechanically stable construction—as small model as possible, so as to be comparable with the dimensions of customary combination electrodes system, can be produced, making possible a broader application of such measuring electrodes, and also including reduced manufacturing costs.

DESCRIPTION OF THE DRAWING

The single drawing shows a longitudinal cut through a measuring probe according to this invention.

ABSTRACT OF THE INVENTION

A measuring probe for measuring the ion concentration in liquid has an enameled steel tube for receiving a reference electrode. The reference electrode is in contact with the liquid through a junction. The reference electrode is contained in an insulating body, one end of which has a mushroomed head. The insulating body is insertable into the steel tube wherein electrical connection is made by a plug-in connection. The mushroom head is external to the steel tube. The reference electrode assembly may be replaced by a blind plug.

DETAILED DESCRIPTION OF THE INVENTION

In the illustrated example a steel tube 1 is enameled on the outside 20, an inside end range 23, and continuously over the edge 22. The tube carrys an ion response enamel measuring electrode 19, which shall be explained in more detail in the following description.

Inserted into the tube-like steel body 1 is a hollow cylindrical body 2 of polytetrafluoroethylene which holds an electrolyte and in which a reference electrode system 10 is arranged in relation with a enameled measuring electrode 19. The end of body 2 contains a junction 11, which may be made of a ceramic material. Body 2 is formed with a mushroomed head 21, the underside of which lies against the enameled edge surface 22 of the tube-like steel body 1. The inside of body 1 is enameled only in the end range 23. At one end of the body 2, a peripheral groove is formed in which is located a sealing O-ring 12. Head 21, being formed like a mushroom, makes possible the simple pulling out and pushing in of the hollow cylindrical body 2 of polytetrafluoroethylene containing the reference electrode system. On the other hand the underside of the head lying against the enameled edge surface 22 guarantees that the particularly impact susceptible end of the enameled steel body 1 is further protected.

The tube-like steel body 1 should consist of a steel suitable for enameling and having very low thermal expansion. Prior to enameling the hole of the tube-like steel body is enlarged at the end for a distance which corresponds with the end range to be enameled on the inside, resulting in a cylindrical internal space along the length of the tube-like steel body after enameling. The hollow cylindrical body 2 of polytetrafluoroethylene 2 may then be easily inserted into the steel body.

The other end of the body 2 is closed by a plug 8 of polytetrafluoroethylene which is sealed off against the cylindrical internal wall of the body 2 by an O-ring 9 and a corresponding ring groove. At this end of the steel body 1 is a metallic threaded insert 5 which is screwed into 1. A contact pin 7 is pressed into 1, which is connected with a socket 17 in the closing plug 8 via a plug connection.

The outside enameling 20 has a section of ion responsive enamel which serves as measuring electrode 19. Electrode 19 is connected with a solder connection 16 via a lead-off 18. The lead-off 18 is formed by a platinum band embedded into the enamel layer 20.

The maximum outside diameter of the enameled tube-like steel body 1 of the illustrated model may be 12.5 mm corresponding with the outside diameter of commercially available glass electrodes. Over the left end of the tube-like steel body 1, which narrows down at that point, an O-ring 6 sealed cover sleeve 4 is set which borders on a covering cap 3, in the front surface of which an O-ring 13 is installed. The covering cap 3 and the cover sleeve 4 are made of appropriate material such as fiberglass reinforced polytetrafluoroethylene. A built-in plug 15 and a screw connection 14, to which a cable is soldered, are arranged in the holes of the cover sleeve and the covering cap, in order to connect the electrodes to a measuring device.

As the reference electrode is installed concentrically inside the tube-like steel body 1, it is screened electrically. The reference electrode can be designed with respect to its potential difference to the measuring electrode in such a manner that the zero point of the electrode system is located at a pH-value of 7 since this is most frequently asked for in practical applications.

In addition to the desired increased mechanical stability a specific advantage of this single rod measuring system in comparison with familiar single rod measuring systems must be seen in the fact that the reference electrodes may be exchanged without difficulties by removing or inserting a relatively cheap reference electrode, or, if so desired, another measuring task may be carried out by using a different type of electrode, such as a redox electrode. Thus a measuring probe according to this invention cannot only be used to replace a single rod measuring system using a glass electrode, but a much broader application is facilitated by the exchangeability of the electrodes. Cost savings are possible compared to a single rod measuring system because the reference electrode, the part which most commonly wears out, cannot be exchanged in the familiar type of single rod measuring system. Furthermore, a blind plug may also be used instead of the reference electrode when using the object of this invention. The electrode used may also be the measuring electrode, so that the enamel electrode then becomes the reference electrode.

I claim:

1. In a measuring probe for determining the ion concentration in liquids, such as for pH-measurements, which includes an enameled tube-like steel body (1) having an external enamel coating (19) serving as a measuring electrode and a reference electrode installed in the tube-like body in a sealed manner, the electrolyte of which is contained in such a manner that the electrolyte is connected with the liquid to be measured via a junction wherein the improvements comprises: said reference electrode comprising an exchangeably installed hollow cylindrical body (2) of an electrically insulating material a reference electrode system (10) contained in the body (2) and a junction (11) in one end of the body (2); the tube-like steel body (1) being coated with enamel in a sealing end range only (23); and a contact (17) provided in the other end of the body (2) in order to connect the reference electrode to an indicating instrument.

2. An improved measuring probe according to claim 1, characterized in that the end of the body (2) containing the junction (11) is formed as a mushroom-like head (21).

3. Measuring probe according to claims 1 or 2, further including an insert (5) in the tube-like steel body (1) and a plug-in connection (7, 17) between insert (5) (1) and the reference electrode.

4. Measuring probe according to claim 1, wherein the length of the internally enameled end range (23) has a larger inner diameter than the rest of the tube-like body (1) prior to enamelling.

5. Measuring probe according to claim 1, wherein a sealing blind plug is interchangeable with the reference electrode.

* * * * *